(12) United States Patent
Garrait et al.

(10) Patent No.: US 6,635,790 B1
(45) Date of Patent: Oct. 21, 2003

(54) PROCESS FOR THE MANUFACTURE OF DEFLUOROMETHANE

(75) Inventors: Dominique Garrait, Millery (FR); Emmanuel Guiraud, Saint Genis Laval (FR)

(73) Assignee: Atofina, Paris LaDefense Cedex (FR)

( * ) Notice: Subject to any disclaimer, the term of this patent is extended or adjusted under 35 U.S.C. 154(b) by 243 days.

(21) Appl. No.: 09/494,125

(22) Filed: Jan. 28, 2000

Related U.S. Application Data

(63) Continuation of application No. 08/838,951, filed on Apr. 23, 1997, now abandoned.

(30) Foreign Application Priority Data

Apr. 29, 1996 (FR) .............................. 96 05369

(51) Int. Cl.⁷ .............................................. C07C 17/08
(52) U.S. Cl. ...................... 570/165; 570/166; 570/167; 570/168; 570/169
(58) Field of Search ................................ 570/165, 166, 570/167, 168, 169

(56) References Cited

U.S. PATENT DOCUMENTS

| | | | | |
|---|---|---|---|---|
| 3,183,276 | A | 5/1965 | Vecchio .................. | 260/653.4 |
| 3,385,794 | A | 5/1968 | Scherer et al. .............. | 252/415 |
| 4,474,895 | A | 10/1984 | Foulletier | |
| 4,579,974 | A | 4/1986 | Cheminal et al. | |
| 4,579,976 | A | 4/1986 | Cheminal et al. | |
| 1,129 | A | 1/1993 | Gumprecht .................. | 570/168 |
| 5,763,708 | A * | 6/1998 | Clemmer et al. ........... | 570/169 |
| 6,242,659 | B1 * | 6/2001 | Requieme et al. .......... | 570/169 |

FOREIGN PATENT DOCUMENTS

| | | | |
|---|---|---|---|
| EP | 55958 | 7/1982 | |
| EP | 486333 | 5/1992 | |
| EP | 546883 | 6/1993 | |
| EP | 648727 | 4/1995 | |
| EP | 657408 | 6/1995 | |
| EP | 657409 | 6/1995 | |
| EP | 751108 | 1/1997 | |
| FR | 2501062 | 9/1982 | |
| FR | 669303 | 1/1995 | ........... C07C/17/38 |
| JP | 49-134612 | 12/1974 | |
| JP | 51-82206 | 7/1976 | |
| JP | 6-263657 | 9/1994 | |
| JP | 5-50953/93 | 9/1994 | |
| WO | WO 94/21579 | 9/1994 | |
| WO | WO 95/12563 | 5/1995 | |
| WO | WO 97/11043 | 3/1997 | |

OTHER PUBLICATIONS

Opposition by Honeywell International Inc. to EP–0805136 in the name of Atofina.

* cited by examiner

*Primary Examiner*—Samuel Barts
*Assistant Examiner*—Elvis O. Price
(74) *Attorney, Agent, or Firm*—Pennie & Edmonds LLP

(57) ABSTRACT

The subject of the invention is a continuous process for the manufacture of difluoromethane (F32) from methylene chloride (F30) and hydrogen fluoride in the presence of chlorine, in the gas phase, over a fluorination catalyst.

Figure 1:
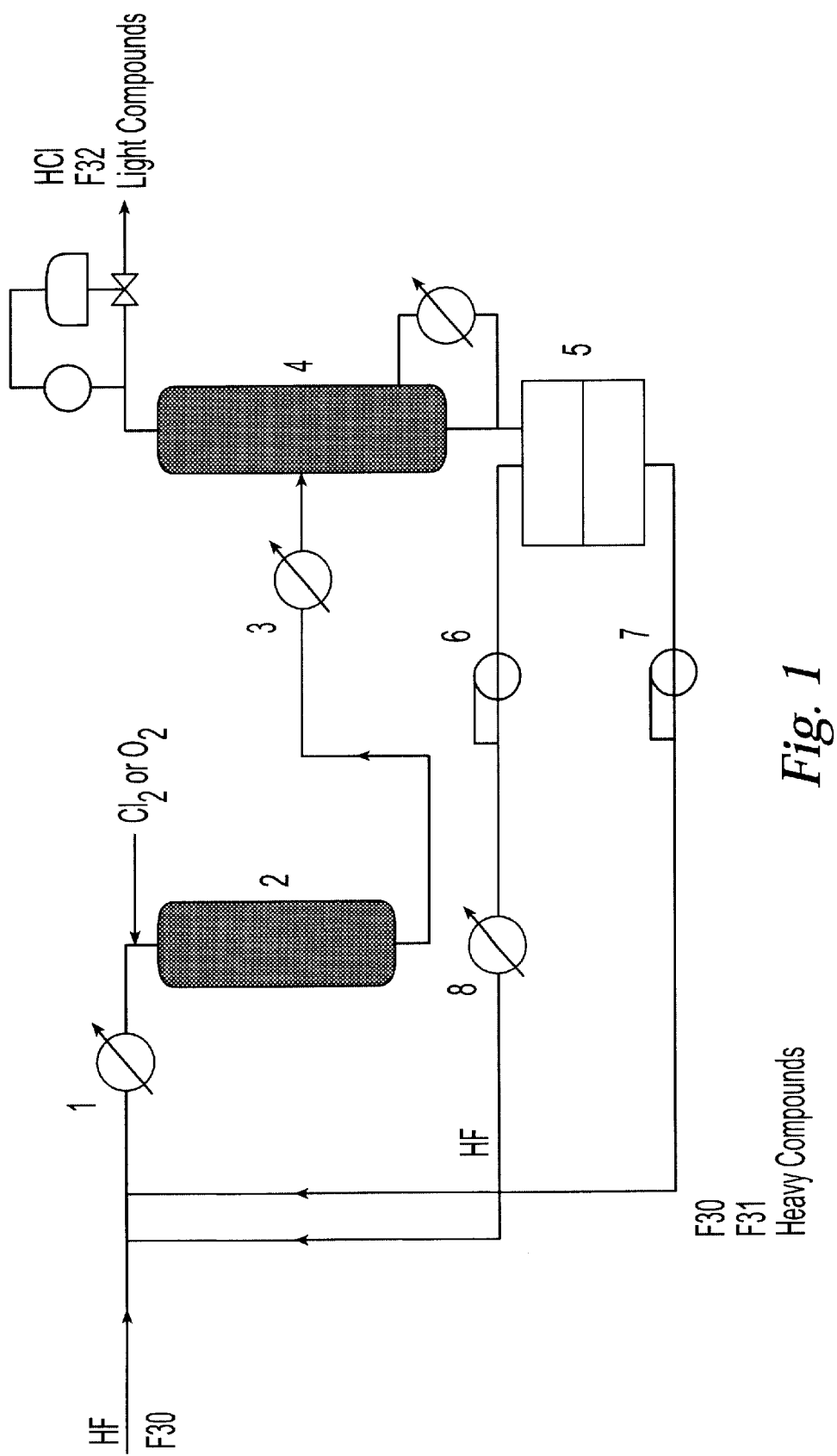

According to the invention, the gas flow exiting from the reactor is subjected to a distillation in order to separate, at the top, a flow containing virtually all the HCl and at least 90% of the F32 produced by the reaction and, at the bottom, a flow containing at least 90% of the unconverted reactants (F31, F30 and HF) and the latter flow is recycled directly to the reactor, without any purification operation.

14 Claims, 1 Drawing Sheet

PROCESS FOR THE MANUFACTURE OF DEFLUOROMETHANE

This application is a continuation of Ser. No. 08/838,951 filed Apr. 3, 1997 now abandoned.

The present invention relates to the field of fluorinated hydrocarbons and has more particularly as subject a continuous process for the manufacture of difluoromethane from methylene chloride and hydrogen fluoride HF.

Now that chlorofluorohydrocarbons (CFCs) have been identified as one of the factors responsible for accelerating the deterioration in the stratospheric ozone layer, politicians and industrialists have been irrevocably committed to a process of substitution of CFCs. This substitution process relates to essential industrial sectors such as the food refrigeration procedure, the insulation of buildings, air conditioning, microelectronics, and the like.

The substitutes envisaged are fluorinated compounds containing hydrogen atoms but not chlorine atoms. One of these compounds, which is without effect on the ozone layer, is difluoromethane, which is known in the trade under the designation F32 and is mainly intended to replaced F22 (chlorodifluoromethane) and R502 (azeotropic mixture of F22 and chloropentafluoroethane) in the field of refrigeration, air conditioning and other applications. There is therefore interest in developing the simplest possible procedure for producing F32 in large and economically competitive amounts.

Access to F32 by the gas phase fluorination of methylene chloride, known in the trade under the designation F30, has already formed the subject of patents claiming the use of catalysts such as $Cr_2O_3$, $CrF_3$, Cr/carbon, $Ni/AlF_3$, and the like.

However, like that of the majority of substitutes for CFCs, the production of F32 poses serious problems because it generates a great many by-products and impurities which, after separation of the HCl and F32, are found either in the recovered HCl and F32 or in the flow to be recycled mainly comprising F30 and F31 (chlorofluoromethane).

In the case of the production of F32 by fluorination of methylene chloride, the most serious problem is posed by the generation, as intermediate compound, of large amounts of highly toxic F31. These contents can be of the order of 20% and it is therefore imperative to limit as far as possible the circulation and the residence time of this compound in the plant, as well as the unit operations involving flows containing F31.

In the catalytic fluorination of F30, the degree of conversion of F30 to F32 is limited by thermodynamics. Typically, for an HF/Organics molar ratio equal to 3 at the inlet of the reactor and a reaction temperature of 300° C., thermodynamic equilibrium corresponds to degrees of conversion of F30 of 65% and of HF of 43%. The flow emerging from the reactor thus mainly contains unconverted reactants (F30, F31 and HF), which it is essential to recycle. To do this, it is possible, in accordance with conventional techniques, to separate and then to purify the main constituents of the flow exiting from the reactor, in particular the unconverted F30, F31 and HF, in order to remove therefrom, before recycling in the reaction, the harmful impurities (such as organic by-products or water) which are generated in the reaction or introduced by the starting materials and which are capable of bringing about-deactivation of the catalyst or of causing corrosion.

During this type of manipulation, the flows to be treated are highly concentrated in F31, which requires reinforcement of the safety measures and equipment and thus an increase in costs.

The direct recycling of the flow of HF, of F30 and of F31 to the reactor after separation of the HCl and F32 produced, without prior purification, has the advantage of limiting the manipulations of flows containing concentrations of F31. This is the reason why the majority of patents describing a process for access to F32 by fluorination of F30 with anhydrous HP in the gas phase mention the direct recycling of the unreacted products (F30, F31 and HF) to the reactor after separation of the HCl and F32 produced (Patent Applications JP 5-50953/93, WO 94/21579 and WO 95/12563).

Moreover, it is known (Patent Applications JP 51-82206 and JP 49-134612) that the continuous injection of oxygen or air or chlorine can increase the lifetime of fluorination catalysts, which have a tendency to become coked or to crystallize very rapidly. However, during the synthesis of F32 in the presence of oxygen, conventionally used to maintain the catalytic activity, the recycling of the crude products to the reactor causes considerable and rapid (less than 100 hours) deterioration in the performance of the catalyst with respect to a recycling-free operation.

It is probably for this reason that the use of oxygen or chlorine for maintaining the activity of the catalyst during the gas-phase fluorination of F30 is not mentioned in any of the patents describing a process for access to F32 by fluorination of F30 with anhydrous HF in the gas phase with direct recycling of the unreacted products (F30, F31 and HF) to the reactor after separation of the HCl and F32 produced.

It has now been found that the injection of chlorine with the reactants (F30 and HF) is not only more effective than the injection of oxygen in stabilizing the catalytic activity but allows, without disadvantage, the direct recycling (without purification) of the flow of unreacted products (F30, F31 and HF).

The subject of the invention is thus a continuous process for the manufacture of F32 from F30 and HF in the gas phase in the presence of a fluorination catalyst, characterized in that the reaction is carried but in the presence of chlorine and in that the gas flow exiting from the reactor is subjected to a distillation in order to separate, at the top, a flow containing virtually all the hydrochloric acid and at least 90% of the F32 produced by the reaction and, at the bottom, a flow containing at least 90% of the unconverted reactants (F30, F31 and HF) present in the gas flow exiting from the reactor and in that the flow recovered at the distillation bottom is recycled directly to the reactor, without any purification operation.

As might have been expected, the recycling of the unconverted reactants directly to the reactor, in the absence of specific purification of the recyclate, results in a certain degree of accumulation of water and of organic by-products in this recyclate. Under stabilized operating conditions, the content of these organic by-products becomes stabilized in a stationary state. Curiously, the nature of these by-products and their content do not hinder the performance of the catalyst:

degree of conversion of F30 similar to the thermodynamic equilibrium state of the reaction $CH_2Cl_2+2HF \rightleftharpoons CH_2F_2+2HCl$ high selectivity for F32, typically of the order of 80 molar %.

In the implementation of the process according to the invention, this performance (activity, selectivity) remains stable for at least 1000 hours; this makes it possible to avoid frequent operations of replacement or regeneration of the catalyst, which operations result in high costs with respect to investment and operating costs. In addition, the process according to the invention is all the more safe in that it does not involve operations of purification of the flow to be recycled and thus production of effluents containing toxic F31.

The fluorination catalyst to be used for the implementation of the process according to the invention can be a bulk catalyst or a supported catalyst, the support stable in the reaction mixture being, for example, an active charcoal, an alumina, a partially fluorinated alumina, aluminium trifluoride or aluminium phosphate. Partially fluorinated alumina is understood to mean a composition which is rich in fluorine and containing mainly aluminium, fluorine and oxygen in proportions such that the amount of fluorine, expressed as $AlF_3$, constitutes at least 50% of the total weight. A catalyst based on chromium is preferably used.

Mention may more particularly be made, among bulk catalysts, of chromium(III) oxide, prepared according to any one of the methods known to the person skilled in the art (sol/gel process, precipitation of the hydroxide from chromium salts, reduction of chromic anhydride, and the like), and chromium trifluoride. The derivatives of metals such as nickel, iron, vanadium (III oxidation state), manganese, cobalt or zinc can also be suitable, alone or in combination with chromium, in the form of bulk catalysts but also in the form of supported catalysts. It is also possible to incorporate, in these catalysts or in their support, alkaline earths, rare earths, graphite or alumina, in order to increase the thermal or mechanical stability thereof. During the preparation of catalysts combining a number of metal derivatives, the catalysts can be obtained by mechanical mixing or by any other technique, such as coprecipitation or coimpregnation.

The supported or bulk catalysts can be employed in the form of balls, extrudates, pellets or even, if the reaction is carried out in a stationary bed, in the form of lumps. When the reaction is carried out in a fluid bed, it is preferable to use a catalyst in the form of balls or extrudates.

Mention may be made, as non-limiting examples of catalysts, of:

chromium oxide microbeads obtained by the sol/gel process as described in Patent FR 2,501,062, catalysts containing chromium oxide deposited on active charcoal (U.S. Pat. No. 4,474,895), on aluminium phosphate (Patent EP 55 958) or on aluminium fluoride (U.S. Pat. Nos. 4,579,974 and 4,579,976), mixed catalysts of chromium oxide and of nickel chloride deposited on aluminium fluoride (Patent Application EP 0,486,333), bulk catalysts based on crystalline chromium oxide (Patent Application EP 657,408), bulk catalysts based on nickel and chromium oxide (Patent Application EP 0,546,883), bulk catalysts based on vanadium and chromium oxide (Patent Application EP 0,657,409).

The abovementioned patents, the contents of which are incorporated here by reference, fully describe the method of preparation of these catalysts but also their method of activation, that is to say of prior conversion of the catalyst into stable active species by fluorination by means of gaseous HF alone or, more generally, mixed with an inert gas such as nitrogen. This treatment is generally carried out for a period of 1 to 24 hours and at a temperature of between 200 and 450° C. During this activation, the metal oxides which act as active material (for example chromium oxide) or as support (for example alumina) can be partially or completely converted to the corresponding fluorides.

The mixed catalyst based on chromium and on nickel described in Patent Applications EP 0,486,333 and EP 0,546,883 are more particularly preferred.

The reaction proper of F30 with HF in the presence of a fluorination catalyst can be carried out in a temperature range of between 220 and 400° C., preferably between 240 and 350° C., with a contact time of between 0.1 second and 60 seconds, preferably from 1 to 20 seconds.

The pressure under which the reaction can be carried out is between atmospheric pressure and 30 bars absolute. The reaction is preferably carried out under a pressure ranging from 10 to 15 bars absolute, which makes it possible economically to carry out the separation of anhydrous HCl from F32.

The amount of hydrogen fluoride used is at least equal to the stoichiometry but the HF/Organics molar ratio in the feed of the reaction is advantageously between 1 and 10, preferably 2 to 5.

With respect to the organics feeding the reaction, the amount of chlorine used to improve the lifetime of the catalyst can vary between 0.1 and 5 molar %. The chlorine can be introduced into the reaction region alone or as a mixture with an inert material, such as nitrogen.

The use of chlorine does not disturb in any way the downstream separation of the reaction and makes it possible to recycle the crude reaction mixture without a fall in activity of the catalyst. A stationary state is achieved which makes it possible to operate in a loop for at least several hundred hours.

The reaction of F30 with HF can be carried out in various types of reactors depending on the catalyst used, its mechanical properties and its resistance to attrition. The reaction can be carried out in a stationary bed or in a fluid bed and in one or a number of reactors. The materials used must be resistant to the corrosion of the mixture and must be, for example, of Inconel or of Hastelloy.

The gas flow exiting from the fluorination reactor mainly comprises HF, F30, F31, F32 and HCl. In accordance with the present invention, this gas flow is subjected to a separation by distillation so as to recover, on the one hand, virtually all the HCl and at least 90% of the F32 present in this flow and, on the other hand, at least 90% of the F30, of the F31 and of the HF, which are directly recycled in the reaction.

This separation can be carried out by distillation in one or two stages, that is to say by separating the HCl and then the F32 or directly, and more simply, in one stage by separating the HCl and the F32 as a mixture. In this case, most of the HCl and of the F32 is obtained at the distillation head and most of the F30 and F31 and of the HF is obtained at the bottom.

This distillation is preferably carried out in a stainless steel column which can be equipped with plates or with packing. The distillation can be carried out under a pressure which can range from 1 to 30 bars absolute, depending on the pressure under which the catalytic fluorination reaction in carried out. The temperature for feeding the reaction mixture can range from 20 to 150° C. The top temperature depends, of course, on the desired separation efficiency and varies as a function of the pressure; it is approximately 0° C. under 12 bars absolute for an F32 purity of greater than 99.5 mol %.

At a set pressure, the top temperature serves to regulate the F31 and HF content of the top flow whereas the boil-up rate at the bottom serves to regulate the removal of the HCl and of the F32. The proportion of HF passing into the top depends essentially on the composition, at the pressure under consideration, of azeotropes formed with F31, F32 and the compounds of the F20 series, such as F22 (chlorodifluoromethane) and F23 (trifluoromethane).

It is observed that, if most of the HCl and at least 90% of the F32 produced in the reaction are not removed, the productivity decreases in the reaction. Likewise, the fact of not separating and recycling directly at least 90% of the F30 and F31 and of the HF which are present at the reaction outlet necessitates, needlessly and dangerously, the reprocessing of these products downstream of the reaction loop.

The reaction and this distillation are preferably carried out under a pressure of between approximately 10 and 15 bars absolute. In fact, under these conditions, the HCl/F32 mixture in itself also separable economically by distillation with production of anhydrous hydrochloric acid. In contrast, at a pressure of the order of 2 to 3 bars absolute, the HCl/F32 mixture resulting from this distillation generally has to be treated with water in order to remove the HCl.

The flow of the unconverted reactants, which is obtained at the bottom of the distillation column, is not subjected to any specific treatment for purification or for removal of organic or inorganic impurities. This flow, mostly composed of F30, of F31 and of HF, thus contains various organic impurities, traces of water (of the order of 1000 ppm by weight or less) and, possibly, a small proportion of non-separated reaction products (F32 and HCl). This flow is directly recycled, after separation by settling, to the fluorination reactor. Fresh reactants (F30 and HF) are, moreover, fed at any point of the reaction/separation/recycling assembly, in proportions which make it possible to compensate for the net production of F32 and of HCl.

The fresh reactants can be introduced either before downstream distillation of the reaction, in order to cool the gases, or into the flow of unconverted reactants recycled in the reaction.

The F31, F30 and HF possibly present as a small proportion in the flow of F32 and of HCl resulting from the distillation head can be subsequently separated from the reaction products by methods known per se and recycled to the reactor.

The following examples illustrate the invention without limiting it. They were carried out on a plant represented in the single appended FIGURE. This plant comprises an Inconel reactor (2) with a working volume of 100 liters and a distillation column (4), made of 316 L stainless steel, having an internal diameter of 150 mm and a height of 6300 mm, which is equipped with a Multiknit 316 L stainless steel packing.

The fresh reactants and the flow of unconverted reactants (recycling) are fed to the reactor after preheating in an electric preheater (1).

HCl, F32 and light products are recovered at the top of the distillation column and F30, F31, HF and heavier products are recovered at the bottom. This flow of unconverted reactants is separated by settling (5) and then recycled to the reactor via two pumps (6) and (7) and an evaporator (8) for the HF phase.

Topping up with fresh F30 and HF is carried out to the feed of the preheater (1), feeding with oxygen or with chlorine is carried out at the inlet of the reactor.

The HF used, of technical grade, has a purity of 99.9 weight % containing, as main impurity, water at a maximum value of 1000 ppm.

The F30 used has a purity of greater than 99.95 weight %.

EXAMPLE 1—COMPARATIVE

The catalyst used is a catalyst based on nickel and on chromium which is supported on fluorinated alumina (content by weight of $AlF_3$ of greater than 78%) prepared by impregnation with chromic acid and nickel chloride hexahydrate and then reduction with methanol. Its main physico-chemical characteristics are as follows:

chemical composition (by weight)
    fluorine: 58.6%
    aluminium: 25.9%
    nickel: 6.4%
    chromium: 6.0% physical properties
    BET specific surface: 52 $m^2/g$
    particle size: balls with a diameter of 1 to 2 mm.

This catalyst was predried and then treated at 300° C. by means of a mixture of hydrogen fluoride and nitrogen.

Fluorination of F30 with this catalyst was carried out, without recycling, under the following operating conditions:

reaction temperature: 250° C.

pressure: 12 bars absolute no recycling contact time: 5 seconds

HF/F30 molar ratio: 3

$Cl_2$/F30 molar ratio in the feed of the reactor: 0.018

The performance observed after 1050 hours under these conditions is as follows:

Conversion of F30 per pass: 62%.

(Conversion is understood to mean the ratio of F30 consumed to F30 entering the reactor).

Selectivity towards F32 per pass: 75 mol %.

(Selectivity towards F32 is understood to mean the molar ratio of F32 produced to F30 consumed).

F32 productivity=1450 g/h/liter of catalyst.

EXAMPLE 2

The reaction is carried out as in Example 1 with a fresh charge of the same catalyst Ni—Cr/$AlF_3$ but with direct recycling of the crude mixture containing most of the unconverted F30, F31 and HF, after separation of the products HCl and F32.

Fluorination of F30 with this catalyst was carried out under the following operating conditions:

a) Reaction reaction temperature: 250° C.

pressure: 12 bars absolute contact time: 4 seconds

HF/Organics molar ratio in the feed of the reactor: 3

$Cl_2$/Organics molar ratio in the feed of the reactor: 0.02 b) Separation

The distillation column intended to process the flow at the outlet of the reactor was adjusted in the following way:

feed temperature ($T_F$): 98° C.

top temperature ($T_T$): 9° C.

heat supplied to the boiler ($Q_B$): 17 kW pressure: 12 bars absolute.

These operating conditions made it possible to obtain, at the top, a flow of F32 and of HCl and, at the bottom, a flow of F30, F31 and HF such that:

the molar F32 and HCl contents of the flow of recycled F30, F31 and HF were less than 1% for F32 and 100 ppm for HCl, the molar F30, F31 and HP contents in the F32 and HCl flow were less than 2000 ppm for F30, 2% for F31 and 2% for HF.

After operating for 1000 hours, the performance observed is as follows:

a) Conversion of F30 per pass: 61%.

b) Selectivity towards F32 per pass: 96%.

The main impurities in the flow of reaction products which is recovered at the top of the distillation column are F23 (2 mol %) and F22 (1 mol %).

c) F32 productivity=1520 g/h/liter of catalyst.

d) Water content in the recycled flow: a number of analyses of the recycled flow were carried out throughout this test in order to determine its water content (Karl Fischer method). The results have shown that there is no accumulation of water and that the $H_2O$ content in the recycled flow was less than 400 ppm by weight.

e) Content of organic impurities in the recyclate: a number of analyses of the recycled flow were carried out throughout this test in order to determine the content of organic impurities in this flow. The results have shown that there was no accumulation and that the content of impurities was stable. This content, expressed as ppm by weight with respect to the total recycled flow, is less than 20000 ppm. The main impurities are F20 (0.2 wt %), F21 (0.1 wt %) F22 (0.3 wt %), F112 (0.5 wt %) and F113 (0.2 wt %).

EXAMPLE 3—COMPARATIVE

The reaction is carried out as in Example 1 with a fresh charge of the same catalyst Ni—Cr/AlF$_3$, without recycling.

Fluorination of F30 with this catalyst was carried out under the following operating conditions:

reaction temperature: 300° C.

pressure: 12 bars absolute contact time: 5 seconds

HF/F30 molar ratio: 3

$O_2$/F30 molar ratio in the feed of the reactor: 0.02

After operating for 400 hours, the performance observed is as follows:

Conversion of F30 per pass: 40%.

Selectivity towards F32 per pass: 59%.

F32 productivity=694 g/h/liter of catalyst.

EXAMPLE 4—COMPARATIVE

The reaction is carried out as in Example 1 with a fresh charge of the same catalyst Ni—Cr/AlF$_3$, with direct recycling of the crude mixture containing most of the unconverted F30, F31 and HF, after separation of the products HCl and F32.

Fluorination of F30 with this catalyst is carried out under the following operating conditions:

a) Reaction reaction temperature: 300° C.

pressure: 12 bars absolute contact time: 8 seconds

HF/Organics molar ratio in the feed of the reactor: 3

$O_2$/organics molar ratio in the feed of the reactor: 0.03 b) Separation

The distillation column intended to process the flow at the outlet of the reactor was adjusted in the following way:

feed temperature ($T_F$): 95° C.

top temperature ($T_T$): 13.5° C.

heat supplied to the boiler ($Q_B$): 16 kW pressure: 12 bars absolute.

These operating conditions made it possible to obtain, at the top, a flow of F32 and of HCl and, at the bottom, a flow of F30, F31 and HF, such that:

the molar F32 and HCl contents of the flow of recycled F30, F31 and HF were less than 1% for F32 and 100 ppm for HCl, the molar F30, F31 and HF contents in the F32 and HCl flow were less than 2000 ppm for F30, 2% for F31 and 2% for HF.

The productivity of Example 3, of the order of 700 g/h/l of F32, could not be achieved. After operating for 60 hours, the performance observed is as follows:

Conversion of F30 per pass: 45%.

Selectivity towards F32 per pass: 96%.

In the flow of reaction products which is recovered at the top of the distillation column, the main impurities were as follows: F23 (1.8 mol %), F22 (0.2 mol %).

Maximum F32 productivity achieved=415 g/h/liter of catalyst.

Water content in the recycled flow: a number of analyses of the recycled flow were carried out throughout this test in order to determine its water content (Karl Fischer method). The results showed that there was no accumulation of water and that the $H_2O$ content in the recycled flow was less than 300 ppm by weight.

Content of organic impurities in the recyclate. The analyses showed that there was an accumulation of impurities in the loop. This content is greater than 3 wt % after 100 hours of operation. The main impurities are the F20 series, F130 and F131.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. A continuous process for the manufacture of difluoromethane (F32) from methylene chloride (F30) and hydrogen fluoride (HF) in the gas phase in a reactor in the presence of a fluorination catalyst, comprising:

carrying out a reaction in the presence of chlorine, wherein the gas flow exiting from the reactor is subjected to a distillation to separate, at the top, a flow containing virtually all the hydrochloric acid and at least 90% of the F32 produced by the reaction, and at the bottom, a flow containing at least 90% of the unconverted reactants F30, chlorofluoromethane (F31) and HF present in the gas flow exiting from the reactor, and the flow recovered at the distillation bottom is recycled directly to the reactor, wherein the HF/organics molar ratio at the reaction inlet is between 1 and 10.

2. The process according to claim 1, wherein the reaction and distillation are carried out under a pressure ranging from 1 to 30 bars absolute.

3. The process according to claim 1, wherein the reaction and distillation are carried out under a pressure of between approximately 10 and 15 bars absolute.

4. The process according to claim 1, wherein a bulk or a supported catalyst based on chromium is used.

5. The process according to claim 1, wherein the fluorination reaction is carried out at a temperature of between 220 and 400° C.

6. The process according to claim 1, wherein the fluorination reaction is carried out at a temperature of between 240 and 350° C.

7. The process according to claim 1, wherein the contact time is between 0.1 and 60 seconds.

8. The process according to claim 1, wherein the contact time is between 1 and 20 seconds.

9. The process according to claim 1, wherein 0.1 to 5 moles of chlorine per 100 mol of organics enters at the reaction inlet.

10. The process according to claim 5, wherein the temperature is between 240 and 350° C.

11. The process according to claim 7, wherein the contact time is between 1 and 20 seconds.

12. A continuous process for the manufacture of difluoromethane (F32) from methylene chloride (F30) and hydrogen fluoride (HF) in the gas phase in a reactor in the presence of a fluorination catalyst, comprising:

carrying out the reaction in the presence of chlorine, wherein the gas flow exiting from the reactor is subjected to a distillation to separate, at the top, a flow containing virtually all the hydrochloric acid and at least 90% of the F32 produced by the reaction, and at the bottom, a flow containing at least 90% of the unconverted reactants F30, chlorofluoromethane (F31) and HF present in the gas flow exiting from the reactor and the flow recovered at the distillation bottom is recycled as a recyclate directly to the reactor; and wherein there is an accumulation of water and of organic by-products in the recyclate which stabilizes without hindering the catalyst; and wherein the reaction is carried out under a pressure ranging from 1 to 30 bars absolute, at a temperature of between 220 and 400° C., with a contact time between 0.1 and 60 seconds, with a HF/organics molar ratio at the reaction inlet between 1 and 10, and with 0.1 to 5 mol of chlorine per 100 mol of organics at the reaction inlet.

13. A continuous process for the manufacture of difluoromethane (F32) from methylene chloride (F30) and hydrogen fluoride (HF) in the gas phase in a reactor in the presence of a fluorination catalyst, comprising:

carrying out the reaction in the presence of chlorine, the gas flow exiting from the reactor is subjected to a distillation to separate, at the top, a flow containing virtually all the hydrochloric acid and at least 90% of the F32 produced by the reaction, and at the bottom, a flow containing at least 90% of the unconverted reactants F30, chlorofluoromethane (F31) and HF present in the gas flow exiting from the reactor and the flow recovered at the distillation bottom is recycled directly to the reactor, wherein the reaction is carried out with an HF/organics molar ratio of between 2 and 5 entering at the reaction inlet.

14. The process according to claim 13, wherein the reaction is carried out with an HE/organics molar ratio of 3 entering at the reaction inlet.

* * * * *

UNITED STATES PATENT AND TRADEMARK OFFICE
CERTIFICATE OF CORRECTION

PATENT NO.    : 6,635,790 B1
DATED         : October 21, 2003
INVENTOR(S)   : Dominique Garrait and Emmanuel Guiraud It is certified that error appears in the above-identified patent and that said Letters Patent is hereby corrected as shown below:

<u>Title page, Item [54] and Column 1, line 2,</u>
Title, replace "DEFLUOROMETHANE" with -- DIFLUOROMETHANE --.

Signed and Sealed this

Thirtieth Day of December, 2003

JAMES E. ROGAN
*Director of the United States Patent and Trademark Office*